(12) United States Patent
Sleat

(10) Patent No.: US 7,330,842 B2
(45) Date of Patent: Feb. 12, 2008

(54) EXPERT SYSTEM PLATFORM

(75) Inventor: Christopher W. Sleat, Annapolis, MD (US)

(73) Assignee: Inclinix, Inc., Wilmington, NC (US)

( * ) Notice: Subject to any disclaimer, the term of this patent is extended or adjusted under 35 U.S.C. 154(b) by 283 days.

(21) Appl. No.: 10/888,388

(22) Filed: Jul. 9, 2004

(65) Prior Publication Data

US 2005/0010544 A1    Jan. 13, 2005

Related U.S. Application Data

(60) Provisional application No. 60/485,758, filed on Jul. 10, 2003.

(51) Int. Cl.
*G06N 5/00* (2006.01)
(52) U.S. Cl. .................. 706/45; 706/47; 702/181; 356/432
(58) Field of Classification Search ............ 600/300; 706/45, 47; 702/181; 356/432
See application file for complete search history.

(56) References Cited

U.S. PATENT DOCUMENTS 4,872,122 A * 10/1989 Altschuler et al. .......... 356/432
5,005,143 A * 4/1991 Altschuler et al. .......... 702/181
5,737,494 A * 4/1998 Guinta et al. ................ 706/47
5,935,060 A * 8/1999 Iliff .............................. 600/300
6,730,027 B2 * 5/2004 Iliff .............................. 600/300

* cited by examiner

*Primary Examiner*—Wilbert L Starks, Jr.
(74) *Attorney, Agent, or Firm*—MacCord Mason PLLC

(57) ABSTRACT

An expert system platform supporting multiple and customizable taxonomies is useable in a number of applications. In one embodiment, the expert system platform includes a plurality of libraries and a plurality of study tables with each being related to a corresponding library. Each of the plurality of libraries corresponds to one of the number of applications and has a question table having a plurality of questions and an answer table having a plurality of answers, each of the plurality of answers is related to one of the plurality of questions, wherein a user of the expert system qualifies for one or more studies or clinical trials based on responses provided by the user. In another embodiment, the expert platform system is useable to identify an individual's potential exposure to chemical, biological, and/or nuclear contamination in a rapidly changing environment.

30 Claims, 3 Drawing Sheets

EXPERT SYSTEM PLATFORM

CROSS-REFERENCE TO RELATED PATENT APPLICATION

This application claims the benefit, pursuant to 35 U.S.C. § 119(e), of provisional U.S. patent application Ser. No. 60/485,758, filed Jul. 10, 2003, entitled "EXPERT SYSTEM PLATFORM," which is incorporated herein by reference in its entirety.

FIELD OF THE INVENTION

The present invention generally relates to an expert system platform, and in particular to the creation and/or utilization of multiple taxonomy libraries that enable mobile and/or stationary users to quickly and accurately navigate through the libraries to perform diagnostics, obtain meaningful information, and provide trend analysis.

BACKGROUND OF THE INVENTION

Many expert systems are based on a question-answer taxonomy platform. In these systems, questions are generated by the system and presented to an end-user. The end-user provides the system with answers to the questions. Generally, the response to the first question determines which question will next be presented to the end-user. The response to the second question determines the third question, and so forth.

There are many known applications of question-answer taxonomy expert systems. One example of a question-answer taxonomy expert system is a medical diagnostic system, in which the questions are intended to obtain information about symptoms a person may be experiencing in order to provide a diagnosis or suggest a treatment plan. The end-user in these systems may be the person experiencing the symptoms, or the end-user may be a trained medical professional providing information to the expert system based on observable events or phenomena, or based on an interview with a patient.

However, these known systems are typically relatively static. In other words, questions and answers in the taxonomy, as well as possible diagnoses and treatments, are not updated or added very frequently. Known systems are therefore not adequate for use in situations in which the taxonomy changes frequently, or changes to the taxonomy need to be made in real-time to account for rapidly changing circumstances.

Known expert systems are typically used in controlled situations, such as a hospital or doctor's office, or on a home computer to perform self-diagnosis. However, there are many situations in which dynamic analysis provided by an expert system would be very beneficial. In addition, there is a need for an expert system that can be used in a remote location, and in situations in which data and patient information is rapidly changing or dynamically evolving, such as during an emergency or crisis situation.

In addition, although known question-answer taxonomy expert systems may be based on very similarly structured taxonomies, typically the taxonomy platform for each system is developed independently. A single expert system platform that can support multiple, customizable taxonomies for use in different applications would be very advantageous.

Although expert systems can collect a large amount of information, known expert systems typically do not provide for any type of analysis of the information obtained, much less dynamic analysis.

Therefore, a heretofore unaddressed need exists in the art to address the aforementioned deficiencies and inadequacies.

SUMMARY OF THE INVENTION

In one aspect, the present invention relates to an expert system platform supporting multiple and customizable taxonomies for use in a number of applications. In one embodiment, the expert system platform includes a plurality of libraries. Each of the plurality of libraries corresponds to one of the number of applications and includes a question table and an answer table. The question table has a plurality of questions that is related to the corresponding application. The plurality of questions is categorized in terms of a ground question, branch questions, and final questions. The branch questions are grouped into N levels, where N is an integer greater than 0. The answer table has a plurality of answers. Each of the plurality of answers corresponds to one of the plurality of questions.

In one embodiment, the question table and the answer table are related such that when the ground question is asked, an answer to the ground question triggers one of the branch questions in level 1 to be asked, when the triggered branch question in level 1 is asked, an answer to the triggered branch question in level 1 triggers one of the final questions or one of the branch questions in level 2 to be asked, when the triggered branch question in level 2 is asked, an answer to the triggered branch question in level 2 triggers one of the final questions or one of the branch questions in level 3 to be asked, and so forth. When one of the branch questions in level N is triggered to be asked, an answer to the triggered branch question in level N triggers one of the final questions to be asked. When one of the final questions is asked, an answer to the one of the final questions triggers one of the remaining final questions to be asked, and so forth, until a last one of the remaining final question is triggered to be asked. An answer to the last final question triggers none of the final questions and none of the branch questions to be asked. A thread of the ground question down through the answer to the last final question constructs a question-answer path associated with the answer to the last final question in the corresponding library.

In one embodiment, a plurality of questions in one of the plurality of libraries is associated with a state of a target of interest. The state, in one embodiment, is related to a type of diseases. In another embodiment, the state is related to a degree of the type of diseases. In an alternative embodiment, the state is related to symptoms of exposure to chemical agents, biological agents, nuclear materials, or any mixture thereof.

Furthermore, the expert system platform includes a plurality of study tables. Each of the plurality of study tables is associated with one of the plurality of libraries and has a number of studies. Each of the number of studies is related to at least one question-answer path in a corresponding library such that when an answer to the last final question is selected, one or many of the number of studies related to the question-answer path associated with the answer to the last final question is displayed.

In one embodiment, the plurality of libraries and the plurality of study tables are stored in a memory device associated with a central host computer that is coupled to and in communication with a network. The plurality of libraries and the plurality of study tables are accessed over the network from a client computer that is coupled to and in communication with the network. In one embodiment, the client computer includes one of a desk computer, a laptop, a personal digital assistant (hereinafter "PDA"), and the like. The network includes at least one of a public network, a dedicated network, a local network, and any combination of them. The public network, in one embodiment, includes the Internet. In an alternate embodiment, for clients that are not web-browser clients, the resulting taxonomies are stored locally on the client computer and do not require a live network connection to use the library once it is set up on the server or computer to match individuals to studies or agents.

Moreover, the expert system platform has a user interface in communication with the plurality of libraries and the plurality of study tables, respectively, for implementing a number of applications. The user interface has a web-based graphic user interface tool. In one embodiment, the user interface includes a client page for collecting information from a target of interest and displaying results based on the information collected from the target of interest. The displayed results comprise details of studies available to the target of interest. The displayed results, in one embodiment, are downloadable.

Preferably, in many embodiments, the user interface includes an administration page for configuring, tuning and/or updating the expert system platform. Also, preferably, the user interface includes a study management page for adding, deleting and/or updating the plurality of study tables.

In another aspect, the present invention relates to a method for building an expert system platform supporting multiple and customizable taxonomies for use in a number of applications. In one embodiment, the expert system platform is implemented as a distributed system associated with a central host computer that is coupled to and in communication with a network. The network comprises at least one of a public network, a dedicated network, a local network, and any combination of them.

In one embodiment, the method includes the step of creating a library for each of the number of applications. The step of creating a library comprises the step of creating a question table having a plurality of questions related to the corresponding application. The plurality of questions is categorized in terms of a ground question, branch questions, and final questions, where the branch questions are grouped into N levels, N being an integer greater than 0. The step of creating a library further comprises the step of creating an answer table having a plurality of answers. Each of the plurality of answers corresponds to one of the plurality of questions. Additionally, the step of creating a library comprises the step of relating the created answer table to the created question table such that when the ground question is asked, an answer to the ground question triggers one of the branch questions in level 1 to be asked, when the triggered branch question in level 1 is asked, an answer to the triggered branch question in level 1 triggers one of the final questions or one of the branch questions in level 2 to be asked, when the triggered branch question in level 2 is asked, an answer to the triggered branch question in level 2 triggers one of the final questions or one of the branch questions in level 3 to be asked, and so forth. When one of the branch questions in level N is triggered to be asked, an answer to the triggered branch question in level N triggers one of the final questions to be asked, and when one of the final questions is asked, an answer to the one of the final questions triggers one of the remaining final questions to be asked, and so forth, until a last one of the remaining final question is triggered to be asked. An answer to the last final question triggers none of the final questions and none of the branch questions to be asked. A thread of the ground question down through the answer to the last final question constructs a question-answer path associated with the answer to the last final question in the corresponding library.

Furthermore, the method for building an expert system platform includes the steps of creating a study table having a number of studies for the created library, and relating each of the number of studies to at least one question-answer path in the created library such that when an answer to the final question is selected, one or many of the number of studies related to a question-answer path associated with the answer to the final questions is displayed.

Moreover, the method for building an expert system platform includes the steps of updating the created library and the created study table, respectively, creating a user interface in communication with the created library and the created study table, respectively, and accessing the expert system platform over the network from a client computer that is coupled to and in communication with the network.

In one embodiment, the step of accessing the expert system platform includes the steps of presenting to a target of interest a plurality of questions from one of the plurality of libraries selected by the target of interest, collecting answers to the plurality of questions from the target of interest, and reporting details of one or many of a number of studies available to the target of interest.

In yet another aspect, the present invention relates to a computer readable medium or media. In one embodiment, a computer readable medium or media includes a data structure relating multiple and customizable taxonomies to an expert system platform for use in a number of applications, and a user interface in communication with the data structure.

In one embodiment, the data structure includes a plurality of libraries. Each of the plurality of libraries corresponds to one of the number of applications, and includes a question table and an answer table. The question table has a plurality of questions that is related to the corresponding application. The plurality of questions is categorized in terms of a ground question, branch questions, and final questions. The branch questions are grouped into N levels, where N is an integer greater than 0. The answer table has a plurality of answers. Each of the plurality of answers corresponds to one of the plurality of questions. In one embodiment, the question table and the answer table are related such that when the ground question is asked, an answer to the ground question triggers one of the branch questions in level 1 to be asked, when the triggered branch question in level 1 is asked, an answer to the triggered branch question in level 1 triggers one of the final questions or one of the branch questions in level 2 to be asked, when the triggered branch question in level 2 is asked, an answer to the triggered branch question in level 2 triggers one of the final questions or one of the branch questions in level 3 to be asked, and so forth. When one of the branch questions in level N is triggered to be asked, an answer to the triggered branch question in level N triggers one of the final questions to be asked. When one of the final questions is asked, an answer to the one of the final questions triggers one of the remaining final questions to be asked, and so forth, until a last one of the remaining final question is triggered to be asked. An answer to the last final question triggers none of the final questions and none of the branch questions to be asked. A thread of the ground question down through the answer to the last final question constructs a question-answer path associated with the answer to the last final question in the corresponding library.

The data structure further includes a plurality of study tables. Each of the plurality of study tables is associated with one of the plurality of libraries and has a number of studies. Each of the number of studies is related to at least one question-answer path in a corresponding library such that when an answer to the final question is selected, one or many of the number of studies related to a question answer path associated with the answer to the final questions is displayed.

In one embodiment, the user interface is used for updating the expert system platform. In another embodiment, the user interface is used for administrating the expert system platform The user interface is also used for implementing one of the number of applications selected by a target of interest, and reporting results of the corresponding application.

These and other aspects of the present invention will become apparent from the following description of the preferred embodiment taken in conjunction with the following drawings, although variations and modifications therein may be affected without departing from the spirit and scope of the novel concepts of the disclosure.

DETAILED DESCRIPTION OF THE INVENTION

Figure 1:
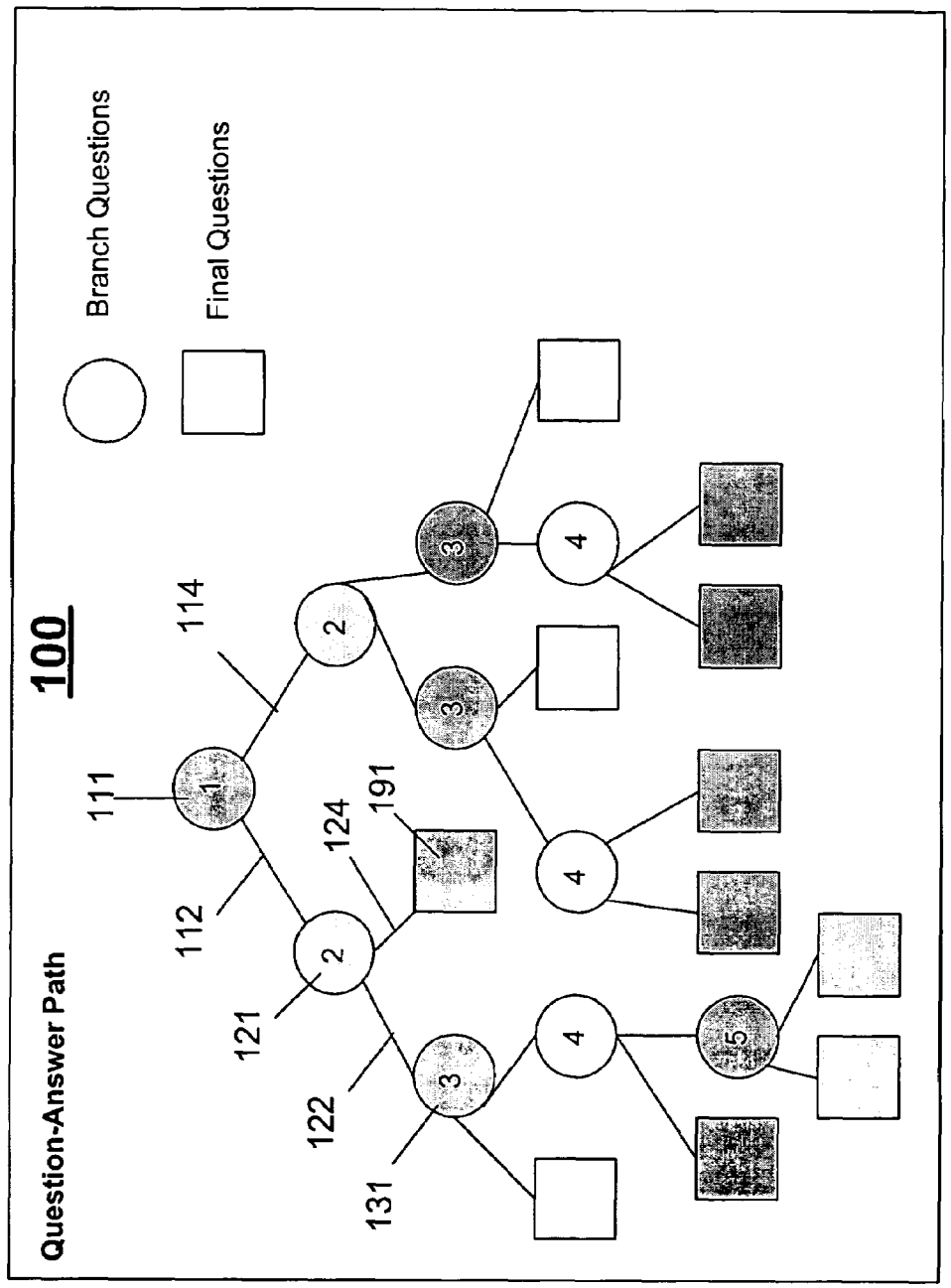
FIG. 1 schematically shows a taxonomy-level diagram of a library according to one embodiment of the present invention.

The present invention is more particularly described in the following examples that are intended as illustrative only since numerous modifications and variations therein will be apparent to those skilled in the art. Various embodiments of the invention are now described in detail. Referring to the drawings, like numbers indicate like parts throughout the views. As used in the description herein and throughout the claims that follow, the meaning of "a," "an," and "the" includes plural reference unless the context clearly dictates otherwise. Also, as used in the description herein and throughout the claims that follow, the meaning of "in" includes "in" and "on" unless the context clearly dictates otherwise.

Figure 2:
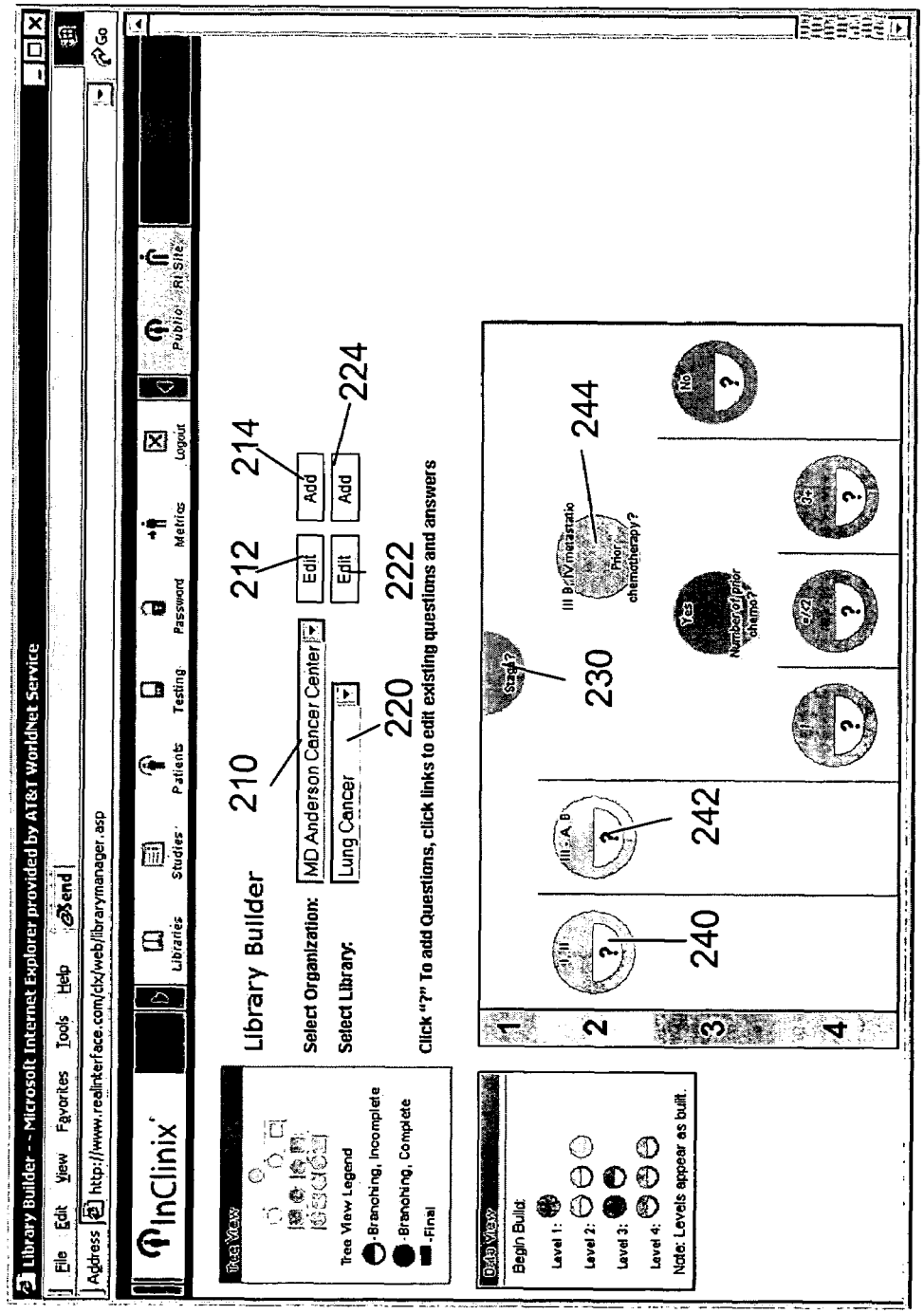
FIG. 2 shows a screen snapshot of a Library Builder according to one embodiment of the present invention.
Figure 3:
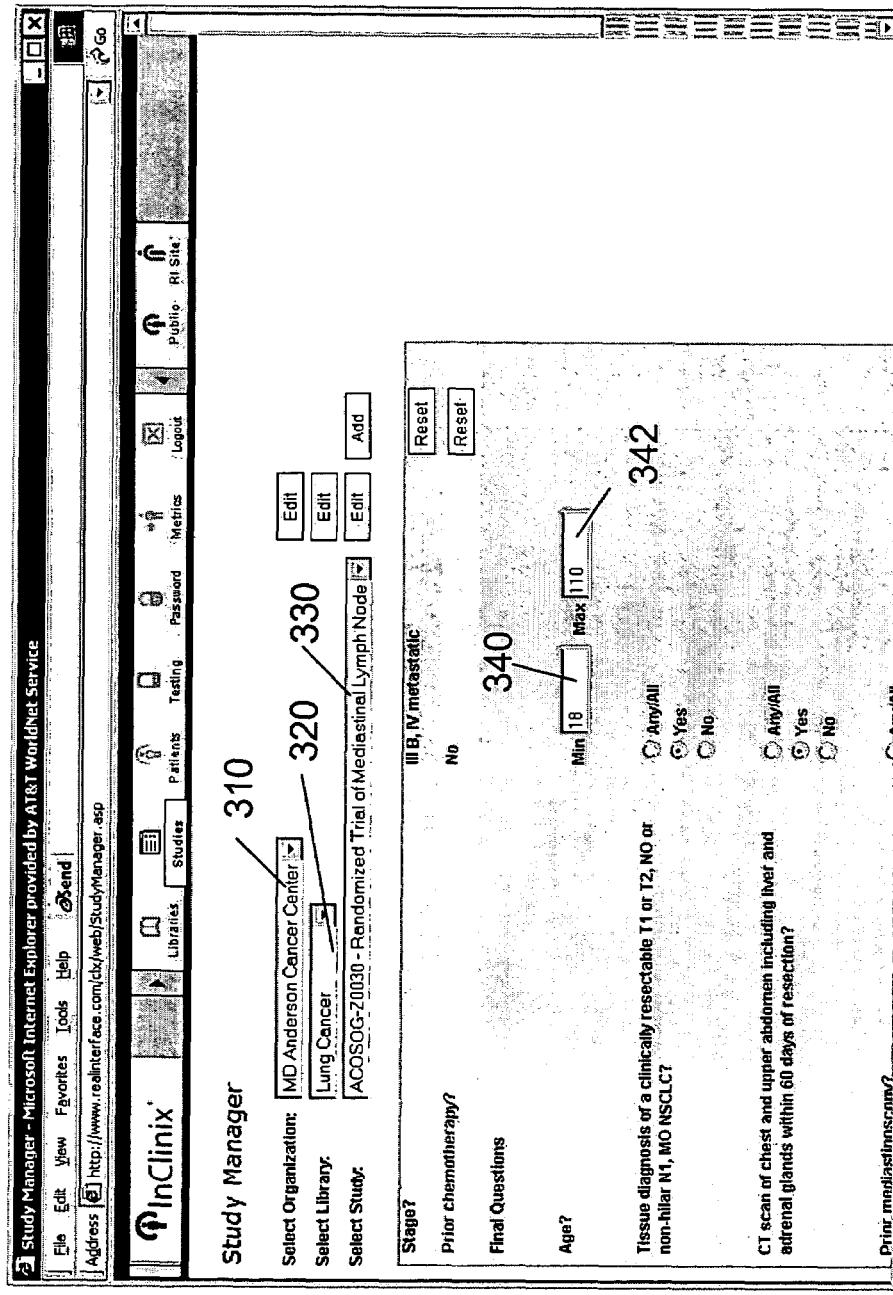
FIG. 3 shows a screen snapshot of a Study Manager according to one embodiment of the present invention.

The description will be made as to the embodiments of the present invention in conjunction with the accompanying drawings, in which like numbers indicate like parts throughout the FIGS. 1-3. In accordance with the purposes of this invention, as embodied and broadly described herein, this invention, in one aspect, relates to a method for building an expert system platform that supports multiple and customizable taxonomies for use in a number of applications.

The number of applications includes a clinical trial screening application that determines whether a patient is qualified for one or more clinical research trials based on the responses of the patient to a plurality of questions, a potential terrorist attack identification system that diagnoses human exposure to hazardous materials using signs and symptoms for exposure to materials covered by material safety data sheets, environmental keys such as smell, viscosity, flame color, color, material types, etc., or mixtures of them, an application that provides diagnostics and trend analysis for emerging infectious diseases, for example, Severe Acute Respiratory Syndrome (SARS), and others.

In a preferred embodiment, taxonomies are implemented using libraries. As described infra, taxonomies are created and maintained using an intuitive web-based graphic user interface (hereinafter "GUI"), and can easily be copied and modified.

In one embodiment, the method for building the expert system platform includes the steps of creating a library for each of the number of applications, creating a study table for the created library, and associating the created study table with the created library so as to quickly and accurately navigate through the library taxonomy to perform diagnostics and obtain meaningful information. Furthermore, the step of creating the library has the steps of creating a question table, creating an answer table, and relating the created answer table to the created question table. The question table has a plurality of questions related to a specific application. The answer table has a plurality of answers. Each of the plurality of answers corresponds to one of the plurality of questions. When each of the plurality of questions and its corresponding answers are created, a unique question identification (hereinafter "ID") associated with the created question and its corresponding answer IDs are created. Meanwhile relationship that respectively associates each of the answers of the created question with the created question, and relationship that dictates a subsequent question associated with one of the answers for each of the answers to the created question are created.

The plurality of questions is categorized in terms of a ground question, branch questions, and final questions. The ground question is a legal verification question. Although the ground question is asked and answered the same every time, the ground question must be asked. Any one of the answers to the ground question will dictate one of the branch questions in level 1 to be asked. For a clinical trial screening application, the ground question is typically whether or not pathology is verified, for example, "Pathology Verified?" The answer to the ground question is multiple choice: "Yes" or "No". Any of the answers to the ground question triggers one of the branch questions in level 1 to be asked. The branch questions are used to eliminate questions to keep a taxonomical process as short as possible. In one embodiment, the branch questions are grouped into N levels, where N is an integer greater than 0. In a preferred embodiment, level 1 contains only one of the branch questions, while subsequent levels may have one or many of the branch questions. An answer to one of the branch questions filters out other possibilities. The final questions are used to determine whether a target of interest (e.g. a patient), can be included or excluded from a study. The final questions could include gender, age, or current medications. The final questions are asked at the end of the taxonomy and answers to the final questions deliver matches to zero, one or more studies.

Specifically, when a branch question in level 1 is asked, an answer to the branch question in level 1 triggers one of the final questions or one of the branch questions in level 2 to be asked, when the triggered branch question in level 2 is asked, an answer to the triggered branch question in level 2 triggers one of the final questions or one of the branch questions in level 3 to be asked, and so forth. When one of the branch questions in level N is triggered to be asked, an answer to the triggered branch question in level N triggers one of the final questions to be asked. When one of the final questions is asked, an answer to the asked final question triggers one of the remaining final questions to be asked, and so forth, until a very last one of the final questions is triggered to be asked. An answer of the last final question triggers no question to be asked. A thread of the ground question down through the answer to the last final question constructs a question answer path associated with the answer to the last final question in the corresponding library taxonomy.

Referring now to FIG. 1, a taxonomy-level diagram 100 is shown according to one embodiment of the present invention. In FIG. 1, each circle represents a branch question, such as questions 111, 121, and 131, and each square indicates a final question such as 191. In this example, the branch questions have 5 levels with each level indicated by 1, 2, 3, 4, or 5 inside a circle. Question 111 has two possible answers with each leading to a separated question-answer path. A straight line 112 connecting question 111 to question 121 in a subsequent level represents an answer to question 111 and an association of the answer with question 121 in the subsequent level. An answer to question 121 will dictate either question 131 or question 191 to be asked next. Selection of answer 122 will dictate question 131 to be asked, while selection of answer 124 will cause question 191 to be asked. Question 191 is a final question which leads the question-answer path to the end. The question-answer path associated with the answer to final question 191 includes question 111, answer 112, question 121, answer 124, question 191 and an answer to question 191.

Adding a question to a library involves updating a question table and a corresponding answer table, respectively, in the library. When a question is added to a library, a question ID of the added question is automatically generated, and a question value, a type and the generated question ID of the added question are written to a question table, respectively. In one embodiment, the question value is a content of the question, and the type is an attribute of the question. For example, for a branch question, the type is Branch; for a final question, the type is FinalNum if the final question is a numeric question while the type is FinalText if the final question is a text question. When an answer to the added question is entered, an answer ID for the entered answer is automatically generated; the answer value and the generated answer ID are respectively written to the question table. This process is repeated for all possible answers to the added question until all the answer values and their associated answer IDs of the answers to the added question are written to the question table. Table 1 is an exemplary question table, which has columns Question ID, Question Value, Answer Value, Answer ID, and Type. For instance, for a question having a Question ID=2 in the exemplary question table, the question value of the question is "Previous Chemo." The question has two answer values corresponding to two possible answers: Yes or No, respectively. For the Yes answer, Answer ID=2A, while Answer ID=2B is assigned for the No answer. The question is a branch question so Type=Branch.

TABLE 1

Question Table Example

| Question ID | Question Value | Answer Value | Answer ID | Type |
|---|---|---|---|---|
| 1 | Gender | Male | 1A | FirstBranch |
|  |  | Female | 1B |  |
| 2 | Previous Chemo | Yes | 2A | Branch |
|  |  | No | 2B |  |
| 3 | Age | Range | 3A | FinalNum |
| 4 | Current Heart Disease | Yes | 4A | FinalText |
|  |  | No | 4B |  |
|  |  | Any/All | 4C |  |

Meanwhile, the answer values, the answer IDs, and the type of the added question are also written to an answer table, respectively. If the added question is a branch question, each of the answers to the added question will dictate a branch question in a subsequent level or a final question. If the added question is a final question, each of the answers to the final question will trigger one of the remaining final questions to be asked or an END flag if the added question is the last final question. An answer to the last final question will lead the taxonomy to the end. Table 2 is an answer table example. The answer table has column Answer ID, Follow-up Question ID, Answer Value, Associated Study ID, Type, and Answer to First Question (Yes/No). Column Follow-up Question ID indicates a question ID of a subsequent question to be asked which is dictated by an answer to a previous question. Column Associated Study ID indicates a study ID of a study case which is associated with a specific answer to a question. For example, an answer having Answer ID=3A will dictate a subsequent question having Follow-up Question ID=4 to be asked. The subsequent question with Follow-up Question ID=4 has three answers with three answer values: 10-88, 44-56 and 33-44, respectively. Each of the three answers is associated with a different study case indicated by an Associated Study ID, for example, the answers 10-88, 44-56, and 33-44 are respectively associated with three studies with Associated Study IDs EE444, RR5534, and 234.

TABLE 2

Answer Table Example

| Answer ID | Follow-up Question ID | Answer Value | Associated Study ID | Type | Answer to First Question (Yes/No) |
|---|---|---|---|---|---|
| 1A | 2 | Male | EE444 RR5534 234 | Branch | Yes |
| 3A | 4 | 10-88 44-56 33-44 | EE444 RR5534 234 | FinalNum | No |
| 4A | 5 | Yes | RR5534 SDFG22 | FinalText | No |
| 4B | 9 | No | RR5534 TT543 |  |  |
| 4C | 11 | Any/All | RR5534 |  |  |
| 11A | End | Yes | 234 | FinalText | No |

Furthermore, the method for building an expert system platform includes the steps of creating a study table having a number of studies for the created library, and relating each of the number of studies to at least one question-answer path in the created library such that when an answer to the final question is selected, one or many of the number of studies related to a question-answer path associated with the answer to the final questions is displayed.

In practice, at first, the expert system platform displays a list of the library names. Selecting one of the libraries leads a corresponding ground question to be asked. Any one of answers to the corresponding ground question will cause a first branch question in level 1 with a question ID is prompted. If the first branch question is a text question, the expert system platform reads answer IDs associated with the first branch question and displays a list of the answer values for the associated answer IDs. When an answer is selected, the expert system platform reads the answer ID of the selected answer and writes associated study IDs for the selected answer to a screened studies table. The screened studies table, in one embodiment, is stored in temporary computer memory (e.g. RAM) and is used advantageously for the screening process.

The expert system platform then reads the follow-up question ID that is associated with the selected answer and displays the follow-up question associated with that question ID. If the follow-up question is a text question, the expert system platform reads the answer IDs associated with the follow-up question and displays a list of the answer values for the associated answer IDs. When an answer is selected, the expert system platform reads the answer ID for the selected answer and then reads the study IDs associated with the answer ID, if any. The expert system platform then compares the study IDs for the selected answer with the study IDs in the screened studies table. If none of the study IDs for the selected answer overlaps with the study IDs in the screened studies table, the expert system platform displays a message stating that there are no matches of studies in the specific question-answer path. If at least one study ID for the selected answer overlaps with the study IDs in the screened studies table, the expert system platform updates the screened studies table with a set of the study IDs for those studies that overlap with the study IDs in the screened studies table. The expert system then reads a follow-up question ID that is associated with the selected answer and prompts the follow-up question. Once an answer to the prompted follow-up question is selected, the expert system platform repeats the process as described above.

If the follow-up question is a numeric question, the expert system platform displays an empty question value box for entry of a numeric value for the question. When an answer value is entered, the system reads the answer ID for the numeric question, and compares the entered answer value with the ranges associated with the answer ID. The expert system platform temporarily records the study IDs for those studies whose associated numeric values match the entered value, then compares the study IDs that are temporarily stored with the study IDs in the screened studies table. If none of the study IDs for the selected answer overlaps with the study IDs in the screened studies table, the expert system platform displays a message stating that there are no matches of studies in the specific question-answer path. If at least one study ID for the selected answer overlaps with the study IDs in the screened studies table, the expert system platform updates the screened studies table with a set of the study IDs for those studies that overlap with the study IDs in the screened studies table. The expert system then reads a follow-up question ID that is associated with the selected answer and prompts the follow-up question.

Once an answer that has Follow-up Question ID=END is selected, the expert system platform compares the study IDs for the selected answer with the study IDs in the updated screened studies table. The overlapped study IDs between the study IDs for the selected answer and the study IDs in the updated screened studies table correspond to those studies that are actual matches. Then the expert system platform displays a list of studies associated with the overlapped study IDs.

The expert system platform of the present invention provides for real-time search results (e.g. diagnoses), real-time information support (e.g. treatment recommendations), and real-time trend analysis (e.g. infectious diseases or biological/chemical attack exposure). The expert system platform, in one embodiment, is preferably implemented as a distributed system, with a client component installed on a client computer device such as a laptop, a personal computer (hereinafter "PC"), PDA, so that an application based on the inventive expert system platform can be used anywhere. The expert system platform preferably implements the taxonomy through libraries, which can be easily and intuitively created and updated, thereby providing for customizable taxonomies. In a preferred embodiment, a web-based GUI is used to visually define a tree structure (similar to FIG. 1) that uses distinct similarities or differences between similar clinical trials to reduce the number of questions required to screen a patient against multiple trials.

These and other aspects of the present invention are more specifically described below in an exemplary embodiment of the expert system platform in use for a clinical trial screening application.

Preferably, to start using the expert system to screen a patient, an end user, or practitioner, needs to install a client portion of the expert system platform into a local computer device that the practitioner will use to implement the patient screening. The local computer device can be a PC, a laptop, a PDA, and the like. The installation includes the following steps: (1) downloading installation files from a central host computer in a server site or from a computer disk in conventional manner to the local computer device, (2) starting installation program, (3) entering the following information into the installation program: organization name, user name and initial password, which are recorded in the server site, (4) changing the initial password, (5) syncing the local computer device, and (6) during the syncing process, downloading the libraries and their associated studies to the local computer device which the end user has permission to use.

For screening a patient who may possibly be included in one of the studies which an organization of the practitioner is involved with, the practitioner "refreshes" the system libraries. The practitioner launches the expert system application on the local computer device. An alphabetical list of the Pathology Libraries available to the practitioner is displayed. The practitioner, for example, selects Thoracic Cancer. A dialog is displayed, which is a ground question, "Pathology Verified? Yes/No". The practitioner selects an answer "Yes", based on information that the patient has provided. The main Thoracic Cancer library page is then displayed, which has a plurality of icons, such as Home, Studies, and Close, and a forward arrow and a reverse arrow. The first branch question is prompted. In this exemplary embodiment, the first branch question is "Stage?" A drop down list box of answers accompanies the question. The three available answers are "I or II", "IIIA/B", and "IIIC or IV". The practitioner selects an answer "IIIC or IV", based on the information that the patient has provided. In one embodiment, the first question and its answer remain on the screen, where the answer displayed is now uneditable. The back arrow becomes available for allowing the practitioner to go back to change a previous answer. A next branch question associated with the selected answer "IIIC or IV" is prompted, which is "Prior Chemo? Yes/No". The practitioner selects an answer "Yes", based on the information that the patient has provided. The previous questions and their answers remain on the screen, where the answers are now uneditable. A next branch question associated with the selected answer "Yes" is asked, which is "Number of treatments?" A drop down list box of the answers accompanies the question. The three available answers are "1", "2", and "3+". The practitioner selects an answer "1", based on the information that the patient has provided. Then all of the final questions are prompted on the screen, which are "Age?" "Gender?" "History of Heart Disease?" and "History of Diabetes?" respectively. The practitioner answers all of the final questions, based on the information that the patient provides.

Based on the answers to these questions, a list of the studies that match the question-answer path (or thread) is displayed. The study names and numbers of the matched studies are displayed as links. By selecting a corresponding upper link, details associated with the study name and the study number are displayed.

The practitioner is able to scroll up and change previous answers, which causes the results and all of the questions following the change to be modified according to the answer.

The practitioner is able to select a "Record" button to record the screening result for the patient. Once finished the patient screening, the practitioner is able to upload the screening results associated with the screened patient to a central database server of the expert system to update the libraries, and to performs a hot sync. During the uploading process, the server checks for updates to the libraries. If the libraries have been updated already, the expert system automatically downloads the updated libraries to the practitioner's local computer device. When the sync process is complete, the updated libraries are available to the practitioner on the practitioner's local computer device.

A system administrator (hereinafter "SA"), or anyone who has a permission of the system administrator, can update studies and their associated libraries, organizations, and user information using a web-based GUI tool from an administration page and/or study management page, which includes a number of management tools, such as Study Manager, Library Builder, and User Manager. To assure that all studies have possible true paths through a library's taxonomy, studies are actually built using a Study Manager Wizard that is made up of the questions used in its associated library.

To create a new library using the Library Builder Wizard, the SA opens a conventional web browser, which is in communication with the central host computer. After logging in, the system displays the Library Builder interface, as shown in FIG. 2. This screen snapshot of the Library Builder, according to one embodiment of the present invention, is merely an example and should not limit the scope of the present invention. One of ordinary skill in the art would recognize other variations, modifications, and alternatives. In the Library Builder page 200 shown in FIG. 2, Select Organization allows the SA to select a desired organization from a drop-down list box 210. The SA selects "MD Anderson Cancer Center" in this example. Edit 212 allows the SA to edit the name of the selected organization and Add 214 allows the SA to add one or more organizations in the list. Select Library allows the SA to select a desired library corresponding to the selected organization from a drop-down list box 320. The SA selects "Lung Cancer" in this example. Edit 222 allows the SA to edit the name of the selected library and Add 224 allows the SA to add one or more libraries for the selected organization.

Then a Question Value box (not shown here) for a branch question in level 1, Answer Type (Text/Numeric) and Number of Answer are automatically displayed. The SA enters the actual question in the Question Value box, and selects a corresponding answer type and number of the answer. In this exemplary embodiment, the SA enters "Stage?" into the Question Value box, and selects "Text" as the answer type and enters 3 as numbers of the answers, then selects "Create Question" to create the first branch question 230. Once the question is created, three Answer IDs are automatically generated. Then three Answer Value boxes with each associated respectively with a different generated answer ID are displayed. The SA enters a corresponding answer value in each of the Answer Value boxes, respectively, and selects "Set Answers & View Trees" to set the answers. As shown in FIG. 2, the three answers to question 230 in the view tree are associated with icons 240, 242 and 244. To associate a subsequent question with a specific answer, the user clicks one of the corresponding icon, 240, 242 or 244. In response, a Question Value box, Question Type (Branch/Final), Answer Type (Text/Numeric), and Number of Answers are displayed. By entering a question value into the Question Value box, selecting a question type in the Question Type (Branch/Final), selecting an answer type in the Answer Type (Text/Numeric), entering a number of the answer to the entered question in the Question Value box, and selecting "Create Question", the subsequent question associated with the specific answer is created. Then Answer Value boxes corresponding to the entered number of the answer are displayed. The SA enters a corresponding answer value in each of the Answer Value boxes, respectively, and selects "Set Answers & View Trees" to set the answers for the subsequent question. Repeating the above process creates a robust library.

To associate a study with a library using the Study Manager Wizard, the SA selects the study management page and then selects the Study Manager. The system displays the Study Manager, as shown in FIG. 3. This snapshot of the Study Manager, according to one embodiment of the present invention, is merely an example and should not limit the scope of the present invention. One of ordinary skill in the art would recognize other variations, modifications, and alternatives. In the Study Manager page 300 shown in FIG. 3, Select Organization allows the SA to select a desired organization from a drop-down list box 310. The SA selects "MD Anderson Cancer Center". Select Library allows the SA to select a desired Library corresponding to the selected organization from a drop-down list box 320. The SA selects "Lung Cancer". Select Study then allows the SA to select a desired study to be associated with the selected library from a drop-down list box 330. The study details include Study Name, Study Number, Study Author, number of Openings, Open Status (Yes/No). In this example, the SA selects "ACOSOG-Z0030—Randomized trial of Mediastinal Lymph Node".

The system displays a branch question in level 1. The question for this exemplary case is, "Stage?" Next to the question, radio buttons (not shown here) for each of the possible answers to the question are displayed: "I or II", "IIIA/B", and "IIIC or IV". The SA checks the answer, "IIIC or IV". Then a question in level 2 that is associated with the answer "IIIC or IV" is displayed, which is, "Prior Chemo?" Next to the question, radio buttons (not shown here) for each of the possible answers to this multiple choice question are displayed: Yes or No. The SA checks "No." The answer dictates the final questions that terminate this path through the Library's taxonomy. One of the final questions for this example is "Age?" which is a numeric question. The SA enters a minimum age 18 and a maximum age 110 to answer entry boxes 340 and 342, respectively, that will make a patient's response match them to the study. Another final question is "Tissue diagnosis of a clinically respectable T1 or T2, NO or non-hilar N1, Mo NSCLC?" which is a multiple choice question with possible answers: Any/All, Yes, or No. The SA selects the answer "Yes". For the final question, "CT scan of chest and upper abdomen including liver and adrenal glands within 60 days of resection?" The SA selects the answer "Yes". The SA makes one or more selections for each of the rest of the final questions. The SA saves the study so as to associate the study to the selected library.

For final questions, an answer "Any/All" is a potential response in addition to the specific answers. The reason for this is because the expert system is blind to which studies are matches with individual patients until the final question is answered and in some cases one or many final question responses may not apply or may not have bearing on the patient's inclusion or exclusion to a study. To associate a study with a library for a final question with the answer "Any/All", the SA selects the answer "Any/All" for the final question. For example, if the SA selects the answer "Any/All" for the final question "CT scan of chest and upper abdomen including liver and adrenal glands within 60 days of resection?" any response given from a client side to the final question matches the specific study. The answer "Any/All" to a final question is not displayed on the client side.

If a study is to be added to a library and additional final questions are required in order to differentiate a new study from others in the library, the additional final questions can be added while configuring the study. However, changing questions in the upper or middle layers of a Library Taxonomy potentially breaks the algorithms for studies already associated with a library. The type of changes is allowed only from the Edit Library page.

A second exemplary application is a potential terrorist attack or infectious disease outbreak identification system. In this application, a plurality of tree structures based on multiple methodologies are used to identify exposure of potential victims to weapons of mass destruction (hereinafter "WMD"), such as a biological agent or chemical agent attack. The application associates known WMD agents to any of the tree structures. New agents and infectious diseases are added in real-time, thereby providing current information to the end-users. Taxonomy questions regarding signs and symptoms of a WMD attack are also added and updated in real-time. The application screens potential victims in real-time and obtains treatment recommendations in real-time. In a preferred embodiment of the application, individual subscriber organizations are able to upload their own unique reaction protocols on an agent-by-agent basis. The application may be configured to trigger notifications to selected individuals or agencies based on an organization's reaction protocols and uploaded information.

An important feature of this application is the ability to upload potential victim information in real-time to a central database, thereby providing for a real-time trend analysis. The trend analysis of potential victim information allows for a system using the inventive expert system platform to detect that an attack has occurred based on the location and symptoms of potential victims. Analysis of uploaded information may also enable identification of the probable type of attack, and the location and potential exposure of the attack. As information is uploaded and attack determinations are made, updated information including response protocols for the responders and recommended treatments for the potential victims are updated for immediate execution upon download.

A client-side component of a WMD screening application is implementable on a PDA or other handheld computer device used by emergency personnel to enter observed symptoms, obtain a diagnosis and view details of the diagnosis and treatment options, and upload victim information to a server for analysis. The dynamic questionnaire guides the interviewer down the path to victim assessment. The questionnaire result displays possible threats and provides protection and treatment options. The application can ascertain the type of contamination, identify exposed personnel, retrieve and distribute protection, notification and action protocols, quickly distribute data on new agents and threats and collect data on victims, all dynamically, in real-time, while in the field.

A server-side component of a WMD screening application is used by a SA to create and update taxonomies, update agent information, and analyze uploaded victim information. In a preferred embodiment, different organizations can use an application, wherein each organization creates and maintains its own taxonomy libraries. Each stored library can be displayed as a question-answer tree, and can be easily and intuitively built and updated. A library can be copied, so that a new library (taxonomy) can be easily created by making small changes to an existing library.

While there has been shown several and alternate embodiments of the present invention, it is to be understood that certain changes can be made as would be known to one skilled in the art without departing from the underlying scope of the invention as is discussed and set forth above and below. Furthermore, the embodiments described above are only intended to illustrate the principles of the present invention and are not intended to limit the scope of the invention to the disclosed elements.

What is claimed is:

1. An expert system platform supporting multiple and customizable taxonomies for use in a number of applications, comprising:
 a. a library builder interface for creating and updating a plurality of libraries in real-time, each of the plurality of libraries corresponding to one of the number of applications and including:
  i). a question table having a plurality of questions related to the corresponding application, the plurality of questions being categorized in terms of a ground question, branch questions, and final questions, the branch questions being grouped into N levels, N being an integer greater than 0; and
  ii). an answer table having a plurality of answers, each of the plurality of answers corresponding to one of the plurality of questions,
  wherein the question table and the answer table are related such that when the ground question is asked, an answer to the ground question triggers one of the branch questions in level 1 to be asked, when the triggered branch question in level 1 is asked, an answer to the triggered branch question in level 1 triggers one of the final questions or one of the branch questions in level 2 to be asked, when the triggered branch question in level 2 is asked, an answer to the triggered branch question in level 2 triggers one of the final questions or one of the branch questions in level 3 to be asked, and so forth, when one of the branch questions in level N is triggered to be asked, an answer to the triggered branch question in level N triggers one of the final questions to be asked, and when one of the final questions is asked, an answer to the one of the final questions triggers one of the remaining final questions to be asked, and so forth, until a last one of the remaining final question is triggered to be asked, an answer to the last final question triggers none of the final questions and none of the branch questions to be asked, wherein a thread of the ground question down through the answer to the last final question constructs a question-answer path associated with the answer to the last final question in the corresponding library; and b. a study manager interface for creating and updating a plurality of study tables in real-time, each of the plurality of study tables being associated with one of the plurality of libraries and having a number of studies, wherein each of the number of studies is related to at least one question-answer path in a corresponding library such that when an answer to the last final question is selected, at least one of the number of studies related to the question-answer path associated with the answer to the last final question is displayed.

2. The expert system platform of claim 1, wherein the plurality of libraries and the plurality of study tables are stored in a memory device associated with a central host computer that is coupled to and in communication with a network.

3. The expert system platform of claim 2, wherein the plurality of libraries and the plurality of study tables are accessed over the network from a client computer that is coupled to and in communication with the network.

4. The expert system platform of claim 3, wherein the network comprises at least one of a public network, a dedicated network, a local network, and any combination of them.

5. The expert system platform of claim 4, wherein the public network comprises the Internet.

6. The expert system platform of claim 3, wherein the client computer comprises one of a desk computer, a laptop, a personal digital assistant (PDA), and the like.

7. The expert system platform of claim 1, further comprising a user interface in communication with the plurality of libraries and the plurality of study tables, respectively, for implementing one of the number of applications.

8. The expert system platform of claim 7, wherein the user interface comprises a web-based graphic user interface tool.

9. The expert system platform of claim 8, wherein the user interface comprises a client page for collecting information from a target of interest and displaying results based on the information collected from the target of interest.

10. The expert system platform of claim 9, wherein the displayed results comprise details of studies for which the target of interest qualifies.

11. The expert system platform of claim 8, wherein the displayed results are downloadable.

12. The expert system platform of claim 8, wherein the user interface comprises an administration page for configuring, tuning and/or updating the expert system platform.

13. The expert system platform of claim 1, wherein a plurality of questions in one of the plurality of libraries is associated with a state of a target of interest.

14. The expert system platform of claim 13, wherein the state is related to a type of disease.

15. The expert system platform of claim 14, wherein the state is related to a degree of the type of disease.

16. The expert system platform of claim 13, wherein the state is related to symptoms of exposure to chemical agents, biological agents, nuclear materials, or any mixture thereof.

17. A method for building an expert system platform supporting multiple and customizable taxonomies for use in a number of applications, comprising the steps of:
  a. providing a library builder interface for creating and updating a library in real-time for at least one of the number of applications, comprising the steps of:
    i). creating a question table having a plurality of questions related to the corresponding application, the plurality of questions being categorized in terms of a ground question, branch questions, and final questions, the branch questions being grouped into N levels, N being an integer greater than 0;
    ii). creating an answer table having a plurality of answers, each of the plurality of answers corresponding to one of the plurality of questions; and
    iii). relating the created answer table to the created question table such that when the ground question is asked, an answer to the ground question triggers one of the branch questions in level 1 to be asked, when the triggered branch question in level 1 is asked, an answer to the triggered branch question in level 1 triggers one of the final questions or one of the branch questions in level 2 to be asked, when the triggered branch question in level 2 is asked, an answer to the triggered branch question in level 2 triggers one of the final questions or one of the branch questions in level 3 to be asked, and so forth, when one of the branch questions in level N is triggered to be asked, an answer to the triggered branch question in level N triggers one of the final questions to be asked, and when one of the final questions is asked, an answer to the one of the final questions triggers one of the remaining final questions to be asked, and so forth, until a last one of the remaining final question is triggered to be asked, an answer to the last final question triggers none of the final questions and none of the branch questions to be asked, wherein a thread of the ground question down through the answer to the last final question constructs a question-answer path associated with the answer to the last final question in the corresponding library;
  b. providing a study manager interface for creating and updating in real-time a study table having a number of studies for the created library; and
  c. relating each of the number of studies to at least one question-answer path in the created library such that when an answer to the last final question is elected, at least one of the number of studies related to a question-answer path associated with the answer to the last final question is displayed.

18. The method of claim 17, further comprising the step of updating the created library and the created study table, respectively.

19. The method of claim 17, further comprising the step of creating a user interface in communication with the created library and the created study table, respectively.

20. The method of claim 19, wherein the expert system platform is implemented as a distributed system associated with a central host computer that is coupled to and in communication with a network.

21. The method of claim 20, further comprising the step of accessing the expert system platform over the network from a client computer that is coupled to and in communication with the network.

22. The method of claim 21, wherein the network comprises at least one of a public network, a dedicated network, a local network, and any combination of them.

23. The method of claim 21, wherein the step of accessing the expert system platform includes the step of presenting a target of interest with a plurality of questions from one of the plurality of libraries selected by the target of interest.

24. The method of claim 23, wherein the step of accessing the expert system platform includes the step of collecting answers to the plurality of questions from the target of interest.

25. The method of claim 24, wherein the step of accessing the expert system platform includes the step of reporting details of the at least one of the number of studies for which the target of interest qualifies.

26. A computer readable medium or media, comprising:
   a. a data structure relating multiple and customizable taxonomies to an expert system platform for use in a number of applications; and
   b. a library builder interface for creating and updating a plurality of libraries in real-time and a user interface in communication with the data structure, wherein the data structure comprises the plurality of libraries, each of the plurality of libraries corresponding to one of the number of applications, and including
      i). a question table having a plurality of questions related to the corresponding application, the plurality of questions being categorized in terms of a ground question, branch questions, and final questions, the branch questions being grouped into N levels, N being an integer greater than 0; and
      ii). an answer table having a plurality of answers, each of the plurality of answers corresponding to one of the plurality of questions, wherein the question table and the answer table are related such that when the ground question is asked, an answer to the ground question triggers one of the branch questions in level 1 to be asked, when the triggered branch question in level 1 is asked, an answer to the triggered branch question in level 1 triggers one of the final questions or one of the branch questions in level 2 to be asked, when the triggered branch question in level 2 is asked, an answer to the triggered branch question in level 2 triggers one of the final questions or one of the branch questions in level 3 to be asked, and so forth, when one of the branch questions in level N is triggered to be asked, an answer to the triggered branch question in level N triggers one of the final questions to be asked, and when one of the final questions is asked, an answer to the one of the final questions triggers one of the remaining final questions to be asked, and so forth, until a last one of the remaining final question is triggered to be asked, an answer to the last final question triggers none of the final questions and none of the branch questions to be asked, wherein a thread of the ground question down through the answer to the last final question constructs a question-answer path associated with the answer to the last final question in the corresponding library.

27. The computer readable medium or media of claim 26, wherein the data structure further comprises a plurality of study tables, each of the plurality of study tables being associated with one of the plurality of libraries and having a number of studies, wherein each of the number of studies is related to at least one question-answer path in a corresponding library such that when an answer to the last final question is selected, one or many of the number of studies related to a question-answer path associated with the answer to the last final question is displayed.

28. The computer readable medium or media of claim 27, wherein the user interface is used for administrating the expert system platform.

29. The computer readable medium or media of claim 27, wherein the user interface is used for implementing one of the number of applications selected by a target of interest.

30. The computer readable medium or media of claim 29, wherein the user interface is used for reporting results of the corresponding application.

* * * * *